United States Patent
Mitchell

(10) Patent No.: US 11,583,567 B2
(45) Date of Patent: Feb. 21, 2023

(54) COMPOSITIONS INCLUDING PIPERONYL BUTOXIDE AND PYRETHRUM EXTRACT

(71) Applicant: GM Pharmaceuticals, Inc., Arlington, TX (US)

(72) Inventor: Odes W. Mitchell, Arlington, TX (US)

(73) Assignee: GM Pharmaceuticals, Inc., Fort Worth, TX (US)

( * ) Notice: Subject to any disclaimer, the term of this patent is extended or adjusted under 35 U.S.C. 154(b) by 14 days.

(21) Appl. No.: 17/154,834

(22) Filed: Jan. 21, 2021

(65) Prior Publication Data
US 2022/0226417 A1   Jul. 21, 2022

(51) Int. Cl.
| | |
|---|---|
| *A61K 36/899* | (2006.01) |
| *A61K 36/61* | (2006.01) |
| *A61K 36/287* | (2006.01) |
| *A61K 31/36* | (2006.01) |
| *A61K 31/22* | (2006.01) |
| *A61K 47/10* | (2017.01) |
| *A61K 36/889* | (2006.01) |
| *A61K 31/355* | (2006.01) |
| *A61K 47/14* | (2017.01) |
| *A61K 47/22* | (2006.01) |
| *A61K 47/32* | (2006.01) |
| *A61K 31/045* | (2006.01) |

(52) U.S. Cl.
CPC ......... *A61K 36/899* (2013.01); *A61K 31/045* (2013.01); *A61K 31/22* (2013.01); *A61K 31/355* (2013.01); *A61K 31/36* (2013.01); *A61K 36/287* (2013.01); *A61K 36/61* (2013.01); *A61K 36/889* (2013.01); *A61K 47/10* (2013.01); *A61K 47/14* (2013.01); *A61K 47/22* (2013.01); *A61K 47/32* (2013.01)

(58) Field of Classification Search
CPC .... A61K 36/899; A61K 31/045; A61K 31/22; A61K 31/355; A61K 31/36; A61K 36/287; A61K 36/61; A61K 36/889; A61K 47/10; A61K 47/14; A61K 47/22; A61K 47/32
See application file for complete search history.

(56) References Cited

FOREIGN PATENT DOCUMENTS

| WO | WO-2002089584 A1 | * | 11/2002 | |
| WO | WO-2014146058 A1 | * | 9/2014 | ............. A01N 31/02 |
| WO | WO-2018107284 A1 | * | 6/2018 | ............. A01N 53/00 |

* cited by examiner

*Primary Examiner* — Robert A Wax
*Assistant Examiner* — Quanglong N Truong
(74) *Attorney, Agent, or Firm* — Winstead PC

(57) ABSTRACT

In an embodiment, the present disclosure pertains to a lice-treating gel composition. In some embodiments, the composition includes piperonyl butoxide with a concentration from about 0.5 to 5 wt/wt %, pyrethrum with a concentration from about 0.1 to 1 wt/wt %, citronella with a concentration from about 0.1 to 1 wt/wt %, lemongrass oil with a concentration from about 0.01 to 0.5 wt/wt %, and tea tree oil with a concentration from about 0.01 to 0.5 wt/wt %. In an additional embodiment, the present disclosure pertains to a lice-treating gel composition including piperonyl butoxide with a concentration of about 3.889 wt/wt %, pyrethrins with a concentration of about 0.6 wt/wt %, citronella with a concentration of about 0.66 wt/wt %, lemongrass oil with a concentration of about 0.14 wt/wt %, and tea tree oil with a concentration of about 0.1 wt/wt %.

9 Claims, No Drawings

COMPOSITIONS INCLUDING PIPERONYL BUTOXIDE AND PYRETHRUM EXTRACT

TECHNICAL FIELD

The present disclosure relates generally to piperonyl butoxide and pyrethrum extract and more particularly, but not by way of limitation, to compositions including piperonyl butoxide and pyrethrum extract.

BACKGROUND

This section provides background information to facilitate a better understanding of the various aspects of the disclosure. It should be understood that the statements in this section of this document are to be read in this light, and not as admissions of prior art.

Lice are tiny, wingless, parasitic insects that feed on blood. Lice are easily spread through close personal contact, sexual contact, sharing personal belongings, and storing personal belongings in close proximity. In general, there are three types of lice: (1) head lice which are found on the scalp; (2) body lice which typically live in clothing and on bedding, and move onto the skin; and (3) pubic lice, commonly called crabs or crab lice, which are found on the skin and hair of the pubic area and, less frequently, on coarse body hair, such as chest hair, eyebrows, eyelashes, and the like.

Common signs and symptoms of lice include, without limitation, intense itching on the scalp, body or genital areas, tickling feeling from movement of hair, visible identification of lice on the scalp, body, clothing or other body hair, visible identification of lice eggs (nits) on hair shafts, sores on the scalp, neck and shoulders, or visible bite marks. Infestation of lice leads to scratching the infected region that typically leads to small red bumps that can become infected with, for example, bacteria or fungi. As such, lice infestations should be promptly treated. Unless treated properly, these conditions can become worse and further result in recurring problems associated with lice infestation. Various embodiments of the present disclosure seek to provide for the treatment of head lice, crab lice, and body lice.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, the present disclosure pertains to a lice-treating gel composition. In some embodiments, the composition includes piperonyl butoxide with a concentration from about 0.5 to 5 wt/wt %, pyrethrum with a concentration from about 0.1 to 1 wt/wt %, citronella with a concentration from about 0.1 to 1 wt/wt %, lemongrass oil with a concentration from about 0.01 to 0.5 wt/wt %, and tea tree oil with a concentration from about 0.01 to 0.5 wt/wt %.

In an additional embodiment, the present disclosure pertains to a lice-treating gel composition including piperonyl butoxide with a concentration of about 3.889 wt/wt %, pyrethrins with a concentration of about 0.6 wt/wt %, citronella with a concentration of about 0.66 wt/wt %, lemongrass oil with a concentration of about 0.14 wt/wt %, and tea tree oil with a concentration of about 0.1 wt/wt %.

In a further embodiment, the present disclosure pertains to a lice-treating gel composition including piperonyl butoxide 90% with a concentration of about 3.889 wt/wt %, pyrethrins 50% (pyrethrum extract) with a concentration of about 0.6 wt/wt %, citronellyl acetate with a concentration of about 0.66 wt/wt %, lemongrass oil with a concentration of about 0.14 wt/wt %, tea tree oil with a concentration of about 0.1 wt/wt %, isopropyl alcohol 70% with a concentration of about 1.425 wt/wt %, coconut oil with a concentration of about 1 wt/wt %, vitamin E (alpha tocopheryl acetate) with a concentration of about 0.5 wt/wt %, isopropyl myristate with a concentration of about 3.5 wt/wt %, PEG-40 hydrogenated castor oil with a concentration of about 5 wt/wt %, DMDM hydantoin with a concentration of about 0.2 wt/wt %, and Carbopol Ultrez 10 NF with a concentration of about 0.95 wt/wt %.

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

Lice feed on blood and can infest the human head, body, and pubic area. The female louse produces a sticky substance that firmly attaches each egg to the base of a hair shaft. Generally, these eggs hatch in approximately six to nine days. Lice infestations occur by coming into contact with either lice or lice eggs. Typically, lice spread through head-to-head, body-to-body, and sexual contact. Additionally, storing infested clothing in closets, lockers, or on side-by-side hangers, or storing personal items such as pillows, blankets, combs, and stuffed toys in close proximity can permit lice to spread.

Furthermore, items shared among friends or family members that can include, without limitation, clothing, headphones, brushes, combs, hair decorations, towels, blankets, pillows, and stuffed toys can contain lice or lice eggs, which can survive for one to two days off the body. This means that simple actions such as using various items among friends or family members, or lying on a bed or sitting on cloth-covered furniture recently used by someone with lice can cause the spread of lice.

Typically, it is very difficult to prevent lice, especially in children or people in close living quarters. Current products exist that claim to repel lice; however, research is currently inconclusive about the efficacy of these products for long-term prevention. Until more research proves the effectiveness of long-term lice prevention products, the best approach is to take thorough steps to get rid of the lice infestation (including lice eggs) and utilize treatment formulations that have the added benefit of temporarily repelling lice during an outbreak.

In general, pyrethrum (e.g., pyrethrum extract) can be used to treat head lice, body lice, and crab lice infections. Pyrethrum is a natural insecticide derived from *Chrysanthemum cinerariaefolium* flowers, but can also be derived from *C. coccineum* and *C. marshalli* flowers. Pyrethrum is the total extract from the flowers, while pyrethrins are the refined six esters. Pyrethrum is a perennial plant with a daisy-like appearance and white flowers. As pyrethrum possesses insecticidal properties, it can be efficiently used as safe and natural insecticides. In particular, pyrethrum can be used in pesticide formations that are to come into contact with skin, such as, lice treatment formations. Since pyrethrum decomposes rapidly in the environment, pyrethrum has been approved for a wide range of indoor and outdoor uses, including homes, restaurants, broad-scale spraying operations, and organic farms. Pyrethrum is absorbed by the lice and destroys the lice by acting on their nervous systems. Pesticide formations (e.g., lice treatment formulations) can additionally include components to enhance the efficacy of the pyrethrum. Piperonyl butoxide, an organic compound, can be used as a synergist component of pesticide formulations, and despite having limited pesticidal activity of its own, piperonyl butoxide enhances the potency of certain pesticides such as, for example, carbamates, pyrethrum, pyrethrins, pyrethroids, and rotenone. As such, combining piperonyl butoxide with pyrethrum can provide for optimal pesticidal activity against insects, such as, but without limitation, lice.

In addition to pyrethrum and piperonyl butoxide combinations, various other constituents can be used in pesticide formations (e.g., lice treatment formulations) for the treatment of head lice, body lice, and crab lice. For example, citronella, sourced from difference species of *Cymbopogon*, can be utilized as a natural insecticide. Citronella has little to no toxicity to humans when used in topical pesticide formations, and has shown the ability to not only kill head lice, body lice, and crab lice, but also act as an insect repellent leading to successful treatment and prevention for a duration after treatment. Use of lice treatment formulations that also exhibit temporary repellent properties can prove highly advantageous. As Research indicates that citronella is an effective repellent, utilizing pesticide formations (e.g., lice treatment formulations) with citronella could significantly lower the incidence of reinfestations during an outbreak of lice when used in addition to treatment therapy. Citronella can be utilized in various forms, such as, but not limited to, citronellyl acetate or other various extracts and oils.

Furthermore, as the most common symptom of a lice infestation is itching on the infested area, lice treatment formulations can prove beneficial by leveraging the use of pain relievers, antiseptics, antibacterials, antifungals, and anti-inflammatory components to reduce pain, itching and swelling, or infections and wounds related to scratching. For instance, lemongrass oil has anti-inflammatory properties thereby aiding in pain relief caused by inflammation due to a louse bite or constant scratching. In addition to providing relief from inflammation and pain, lemongrass oil further acts as an antibacterial and antifungal agent. Thus, lemongrass oil can be used to prevent bacterial or fungal infections related to lice bites, irritated or damaged skin, and scratching of the infested area. As such, lemongrass oil provides the advantages of reducing risk of bacterial or fungal infections by acting as an antiseptic and reducing pain related to inflammation of damaged skin.

Similar to lemongrass oil, tea tree oil shows antibacterial, antifungal, anti-inflammatory, and antiseptic properties. In addition, research suggests that tea tree oil can kill lice in the nymph and adult stages of life, and furthermore, also reduces the number of lice eggs that hatch during an infestation. Addition research indicated that tea tree oil was found to prevent feeding by lice in treated areas. This indicates that tea tree oil not only provides aid in reducing risk of bacterial or fungal infections by acting as an antiseptic and reducing inflammation of damaged skin, but can also aid in the killing of lice.

In addition to the above-mentioned constituents, various other components can be present within pesticide formations (e.g., lice treatment formulations) to enhance both efficacy and provide for a more robust and easy to use formulation. For example, various thickeners or gelling agents, such as carbomers, can be added to the formulation for ease of use (e.g., forming a gel formulation). Additionally, gelling agents provide for the formulation to be in a gel form allowing for the formulation to stay in the hair longer than traditional shampoos. For example, in some instances the gel formation allows for the gel to stay in the infected hair for periods around 10 minutes. Gel formations additionally allow for an easier application over traditional shampoos and creams, thus having better results in killing lice as the formation stays in the hair longer than traditional products.

Furthermore, emollients, spreading agents, solubilizers, and the like, such as isopropanol and isopropyl myristate can additionally be added to the formulation to provide for softening or soothing of skin, or to provide better absorption into the skin. Similar to emollients, moisturizers such as coconut oil, hydrogenated castor oil, and vitamins (e.g., vitamin E) can also be added to moisturize and/or lubricate the skin of a lice-infested area of skin. In some instances, the moisturizers can further aid in the healing of irritated and/or damaged skin. Various other constituents that are well known to those of ordinary skill in the art are also readily envisioned to provide for ease of handling, formulation consistency, dilution, pH balance/buffering, and the like.

Reference will now be made to more specific embodiments of the present disclosure and data that provides support for such embodiments. However, it should be noted that the disclosure below is for illustrative purposes only and is not intended to limit the scope of the claimed subject matter in any way.

Table 1, shown below, illustrates an example combination of piperonyl butoxide and pyrethrum for lice treatment.

TABLE 1

Primary Lice Killing Components.

| Primary Ingredients | Amount (wt/wt %) |
|---|---|
| Piperonyl Butoxide | 3.50% |
| Pyrethrum Extract | Equivalent to 0.30% Pyrethrins |

In some embodiments, the piperonyl butoxide has a concentration from 1 to 5 wt/wt %. In some embodiments, the pyrethrum extract can be in the form of pyrethrum or pyrethrins. In some embodiments, the pyrethrum extract has a concentration from 0.01 to 1.0 wt/wt %. In some embodiments, the pyrethrum extract has an equivalent concentration of 0.01 to 1.0 wt/wt % pyrethrins.

Table 2, shown below, illustrates an example of secondary ingredients and their corresponding functions that can be used in combination with piperonyl butoxide and pyrethrum for lice treatment.

TABLE 2

Secondary Ingredients Complimentary to Primary Lice Killing Components.

| Secondary Ingredients | Function |
|---|---|
| Carbomer | Thickener/Gelling Agents |
| Citronellyl Acetate | Lice Treatment |
| Coconut Oil | Moisturizer and Antibacterial |
| DMDM Hydantoin | Preservative |

TABLE 2-continued

Secondary Ingredients Complimentary to Primary Lice Killing Components.

| Secondary Ingredients | Function |
|---|---|
| PEG40-Hydrogenated Castor Oil | Moisturizer, Solubilizer, and Lice Killer |
| Isopropanol | Solubilizer and Lice Killer |
| Isopropyl Myristate | Emollient and Spreading Agent |
| Lemongrass Oil | Antiseptic, Pain Reliever, and Fragrance |
| Purified Water | Diluent |
| Sodium Hydroxide | Neutralizer |
| Tea Tree Oil | Antibacterial, Antifungal, Anti-Inflammatory, and Antiseptic |
| Tocopheryl Acetate (Vitamin E) | Moisturizer and Skin Healing |

In some embodiments, the carbomer can include, without limitation, carbomer 934, carbomer 934 P, carbomer 941, carbopol 910, carboxyvinyl polymer, and combinations thereof. In some embodiments, the carbomer can be substituted or combined with other thickeners, gelling agents, and combinations thereof. In some embodiments, citronella can be in a form including, without limitation, citronellyl acetate, citronella oil, Sri Lanka (Ceylon) citronella oil, Java citronella oil, and combinations thereof. In some embodiments, the coconut oil can be substituted or combined with cetyl alcohol, cetearyl alcohol, cocoa butter, isopropyl palmitate, lanolin, liquid paraffin, polyethylene glycols, shea butter, silicone oils, stearic acid, stearyl alcohol, other moisturizers, antibacterials, and combinations thereof. In some embodiments, the PEG40-hydrogenated castor oil can be substituted or combined with sulfated castor oil, black castor oil, other moisturizers, solubilizers, lice killers, and combinations thereof. In some embodiments, the isopropanol can be substituted or combined with polysorbate, caprylyl, capryl glucoside, olive oil, other solubilizers, lice killers, and combinations thereof. In some embodiments, the isopropyl myristate can be substituted or combined with shea butter, cocoa butter, mineral oil, lanolin, petrolatum, paraffin, beeswax, squalene, other emollients, spreading agents, and combinations thereof. In some embodiments, the lemongrass oil can be in the form of natural oils, extracts, synthetic oils, and combinations thereof. In some embodiments, the tea tree oil can be in the form of natural oils, extracts, synthetic oils, and combinations thereof. In some embodiments, the sodium hydroxide can be substituted or combined with potassium hydroxide, ammonium hydroxide, sodium bicarbonate, other neutralizers, pH balancers, buffers, and combinations thereof. In some embodiments, the tocopheryl acetate (vitamin E) can be substituted or combined with natural vitamin E, other vitamins such as vitamins A, B and D, various sources of vitamins A, B, D and E, other moisturizers, skin healers, and combinations thereof.

Table 3, shown below, illustrates an example of a lice killing formulation according to aspects of the present disclosure.

TABLE 3

Lice Killing Formulation.

| Formulation Ingredients | Amount (wt/wt %) |
|---|---|
| Purified Water | 75.000 |
| Isopropyl Alcohol 70% | 1.425 |
| Piperonyl Butoxide 90% | 3.889 |
| Pyrethrins 50% (Pyrethrum Extract) | 0.600 |
| Coconut Oil | 1.00 |

TABLE 3-continued

Lice Killing Formulation.

| Formulation Ingredients | Amount (wt/wt %) |
|---|---|
| Vitamin E (Alpha Tocopheryl Acetate) | 0.500 |
| Isopropyl Myristate | 3.500 |
| PEG-40 Hydrogenated Castor Oil | 5.000 |
| Citronellyl Acetate | 0.660 |
| DMDM Hydantoin | 0.200 |
| Lemongrass Oil | 0.140 |
| Tea Tree Oil | 0.100 |
| Carbopol Ultrez 10 NF | 0.950 |
| Sodium Hydroxide | Adjust the pH to 4.7-5.3 |
| Purified Water | QS to 100% |

In some embodiments, the purified water has a concentration from about 20 to 95 wt/wt %. In some embodiments, the isopropyl alcohol (e.g., isopropyl alcohol 70%) has a concentration from about 0.1 to 2 wt/wt %. In some embodiments, the piperonyl butoxide (e.g., piperonyl butoxide 90%) has a concentration from about 0.5 to 5 wt/wt %. In some embodiments, the pyrethrins (e.g., pyrethrins 50% from pyrethrum extract) have a concentration from about 0.1 to 1 wt/wt %. In some embodiments, the coconut oil has a concentration from about 0.25 to 2 wt/wt %. In some embodiments, the vitamin E (e.g., alpha tocopheryl acetate) has a concentration from about 0.1 to 2 wt/wt %. In some embodiments, the isopropyl myristate has a concentration from about 0.1 to 5 wt/wt %. In some embodiments, the castor oil (e.g., PEG-40 Hydrogenated Castor Oil) has a concentration from about 1 to 10 wt/wt %. In some embodiments, the citronellyl acetate has a concentration from about 0.1 to 1 wt/wt %. In some embodiments, the DMDM hydantoin has a concentration from about 0.05 to 0.75 wt/wt %. In some embodiments, the lemongrass oil has a concentration from about 0.01 to 0.5 wt/wt %. In some embodiments, the tea tree oil has a concentration from about 0.01 to 0.5 wt/wt %. In some embodiments, the Carbopol Ultrez 10 NF has a concentration from about 0.1 to 5 wt/wt %. In some embodiments, the sodium hydroxide has a concentration to provide the formulation with a pH value of 4 to 6. In some embodiments, the purified water is added quantum satis (QS).

In some embodiments, the purified water has a concentration of about 75.000 wt/wt %. In some embodiments, the isopropyl alcohol (e.g., isopropyl alcohol 70%) has a concentration of about 1.425 wt/wt %. In some embodiments, the piperonyl butoxide (e.g., piperonyl butoxide 90%) has a concentration of about 3.889 wt/wt %. In some embodiments, the pyrethrins (e.g., pyrethrins 50% from pyrethrum extract) have a concentration of about 0.600 wt/wt %. In some embodiments, the coconut oil has a concentration of about 1.000 wt/wt %. In some embodiments, the vitamin E (e.g., alpha tocopheryl acetate) has a concentration of about 0.500 wt/wt %. In some embodiments, the isopropyl myristate has a concentration of about 3.500 wt/wt %. In some embodiments, the castor oil (e.g., PEG-40 Hydrogenated Castor Oil) has a concentration of about 5.000 wt/wt %. In some embodiments, the citronellyl acetate has a concentration of about 0.660 wt/wt %. In some embodiments, the DMDM hydantoin has a concentration of about 0.300 wt/wt %. In some embodiments, the lemongrass oil has a concentration of about 0.140 wt/wt %. In some embodiments, the tea tree oil has a concentration of about 0.100 wt/wt %. In some embodiments, the Carbopol Ultrez 10 NF has a concentration of about 0.950 wt/wt %. In some embodiments, the sodium hydroxide has a concentration to provide the formulation with a pH value of 4.7 to 5.3. In some embodiments, the purified water is added QS.

In view of the above, in an embodiment, the present disclosure pertains to a lice-treating gel composition. In some embodiments, the composition includes piperonyl butoxide with a concentration from about 0.5 to 5 wt/wt %, pyrethrum with a concentration from about 0.1 to 1 wt/wt %, citronella with a concentration from about 0.1 to 1 wt/wt %, lemongrass oil with a concentration from about 0.01 to 0.5 wt/wt %, and tea tree oil with a concentration from about 0.01 to 0.5 wt/wt %.

In some embodiments, the piperonyl butoxide is piperonyl butoxide 90%. In some embodiments, the pyrethrum is in the form of pyrethrins 50% (pyrethrum extract). In some embodiments, the citronella is in the form of citronellyl acetate.

In some embodiments, the composition further includes isopropyl alcohol with a concentration from about 0.1 to 2 wt/wt %, coconut oil with a concentration from about 0.25 to 2 wt/wt %, vitamin E with a concentration from about 0.1 to 2 wt/wt %, isopropyl myristate with a concentration from about 0.1 to 5 wt/wt %, castor oil with a concentration from about 1 to 10 wt/wt %, DMDM hydantoin with a concentration from about 0.05 to 0.75 wt/wt %, and a carbomer with a concentration from about 0.1 to 5 wt/wt %.

In some embodiments, the isopropyl alcohol is isopropyl alcohol 70%. In some embodiments, the vitamin E is in the form of alpha tocopheryl acetate. In some embodiments, the castor oil is PEG-40 Hydrogenated Castor Oil. In some embodiments, the carbomer is Carbopol Ultrez 10 NF.

In some embodiments, the composition further includes sodium hydroxide with a concentration to provide the lice-treating gel composition with a pH value of 4 to 6. In some embodiments, the composition further includes purified water in a concentration from about 20 to 95 wt/wt %.

In some embodiments, the concentration of the piperonyl butoxide is about 2.5 wt/wt %. In some embodiments, the piperonyl butoxide is piperonyl butoxide 90% with a concentration of about 3.889 wt/wt %. In some embodiments, the pyrethrum is in the form of pyrethrins 50% (pyrethrum extract) with a concentration of about 0.6 wt/wt %. In some embodiments, the pyrethrum has a concentration equivalent to about 0.3 wt/wt % of pyrethrins. In some embodiments, the citronella is in the form of citronellyl acetate with a concentration of about 0.66 wt/wt %. In some embodiments, the lemongrass oil has a concentration of about 0.14 wt/wt %. In some embodiments, the tea tree oil has a concentration of about 0.1 wt/wt %.

In an additional embodiment, the present disclosure pertains to a lice-treating gel composition including piperonyl butoxide with a concentration of about 3.889 wt/wt %, pyrethrins with a concentration of about 0.6 wt/wt %, citronella with a concentration of about 0.66 wt/wt %, lemongrass oil with a concentration of about 0.14 wt/wt %, and tea tree oil with a concentration of about 0.1 wt/wt %.

In a further embodiment, the present disclosure pertains to a lice-treating gel composition including piperonyl butoxide 90% with a concentration of about 3.889 wt/wt %, pyrethrins 50% (pyrethrum extract) with a concentration of about 0.6 wt/wt %, citronellyl acetate with a concentration of about 0.66 wt/wt %, lemongrass oil with a concentration of about 0.14 wt/wt %, tea tree oil with a concentration of about 0.1 wt/wt %, isopropyl alcohol 70% with a concentration of about 1.425 wt/wt %, coconut oil with a concentration of about 1 wt/wt %, vitamin E (alpha tocopheryl acetate) with a concentration of about 0.5 wt/wt %, isopropyl myristate with a concentration of about 3.5 wt/wt %, PEG-40 hydrogenated castor oil with a concentration of about 5 wt/wt %, DMDM hydantoin with a concentration of about 0.2 wt/wt %, and Carbopol Ultrez 10 NF with a concentration of about 0.95 wt/wt %.

Although various embodiments of the present disclosure have been described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A lice-treating gel composition comprising:
   piperonyl butoxide 90% with a concentration of 3.889 wt/wt %;
   pyrethrins 50% (pyrethrum extract) with a concentration of 0.6 wt/wt %;
   citronella with a concentration of 0.66 wt/wt %;
   lemongrass oil with a concentration of 0.14 wt/wt %; and
   tea tree oil with a concentration of 0.1 wt/wt %.

2. A lice-treating gel composition consisting of:
   piperonyl butoxide 90% with a concentration of 3.889 wt/wt %;
   pyrethrins 50% (pyrethrum extract) with a concentration of 0.6 wt/wt %;
   citronellyl acetate with a concentration of 0.66 wt/wt %;
   lemongrass oil with a concentration of 0.14 wt/wt %;
   tea tree oil with a concentration of 0.1 wt/wt %;
   isopropyl alcohol 70% with a concentration of 1.425 wt/wt %;
   coconut oil with a concentration of 1 wt/wt %;
   vitamin E (alpha tocopheryl acetate) with a concentration of 0.5 wt/wt %;
   isopropyl myristate with a concentration of 3.5 wt/wt %;
   PEG-40 hydrogenated castor oil with a concentration of 5 wt/wt %;
   DMDM hydantoin with a concentration of 0.2 wt/wt %; and
   a carbomer with a concentration of 0.95 wt/wt %.

3. The lice-treating gel composition of claim 1, further comprising isopropyl alcohol 70% with a concentration of 1.425 wt/wt %.

4. The lice-treating gel composition of claim 1, further comprising coconut oil with a concentration of 1 wt/wt %.

5. The lice-treating gel composition of claim 1, further comprising vitamin E (alpha tocopheryl acetate) with a concentration of 0.5 wt/wt %.

6. The lice-treating gel composition of claim 1, further comprising isopropyl myristate with a concentration of 3.5 wt/wt %.

7. The lice-treating gel composition of claim 1, further comprising PEG-40 hydrogenated castor oil with a concentration of 5 wt/wt %.

8. The lice-treating gel composition of claim 1, further comprising DMDM hydantoin with a concentration of 0.2 wt/wt %.

9. The lice-treating gel composition of claim 1, further comprising a carbomer with a concentration of 0.95 wt/wt %.

* * * * *